US007144716B2

(12) United States Patent
Saville

(10) Patent No.: US 7,144,716 B2
(45) Date of Patent: Dec. 5, 2006

(54) RECOVERY METHOD FOR IMMOBILIZED BIOCATALYSTS

(76) Inventor: Bradley A. Saville, University of Toronto, Department of Chemical Engineering and Applied Chemistry, 200 College Street, Toronto, Ontario (CA) M5S 3E5

( * ) Notice: Subject to any disclaimer, the term of this patent is extended or adjusted under 35 U.S.C. 154(b) by 652 days.

(21) Appl. No.: 10/200,166

(22) Filed: Jul. 23, 2002

(65) Prior Publication Data

US 2003/0032084 A1   Feb. 13, 2003

(30) Foreign Application Priority Data

Aug. 2, 2001   (CA)   ................................. 2354782

(51) Int. Cl.
*C12N 9/00*   (2006.01)
(52) U.S. Cl. .................................................. 435/183
(58) Field of Classification Search .................... None
See application file for complete search history.

(56) References Cited

U.S. PATENT DOCUMENTS

| 4,033,820 | A |   | 7/1977  | Brouillard |   |
|-----------|---|---|---------|------------|---|
| 4,158,609 | A |   | 6/1979  | Müller     |   |
| 4,209,591 | A |   | 6/1980  | Hendricks  |   |
| 4,442,216 | A |   | 4/1984  | Harvey et al. |   |
| 4,511,654 | A |   | 4/1985  | Rohrbach et al. |   |
| 4,594,322 | A |   | 6/1986  | Thompson et al. |   |
| 4,698,302 | A | * | 10/1987 | Whitehead et al. | 435/94 |
| 4,840,900 | A | * | 6/1989  | Wasileski  | 435/96 |
| 4,844,809 | A |   | 7/1989  | Yoshiro et al. |   |
| 5,177,005 | A |   | 1/1993  | Lloyd et al. |   |
| 5,348,871 | A | * | 9/1994  | Scott et al. | 435/165 |
| 6,214,617 | B1 | * | 4/2001 | Herman     | 435/394 |
| 6,596,520 | B1 |   | 7/2003  | Friedrich et al. |   |

FOREIGN PATENT DOCUMENTS

| CN | 1070915 A | 4/1993 |
| WO | WO 85/05561 A1 | 12/1985 |
| WO | WO 92/01779 A1 | 2/1992 |
| WO | WO 98/30710 A1 | 7/1998 |
| WO | WO 02/055723 A1 | 7/2002 |

OTHER PUBLICATIONS

P. Seccombe, "Development of a Hydrocyclone Bioreactor For The Continuous Culture of Immobilised Yeast Cells," Journal of Chemical Technology and Biotechnology, vol. 51, No. 2, 1991, pp. 284-285, Fermentation and Microbial Physiology, Chemical Engineering Department, University College of Swansea, Singleton Park, Swansea SA2 8PP, UK.
Knutsen et al, "Ultrafiltration Separation of Cellulase and Glucose for a Lignocellulosic Biomass-to-Ethanol Process," 23 Symposium on Biotechnology for Fuels and Chemicals Abstract Booklet, Poster 5-10, M. Finkelstein & B. Danson, Eds. May 6-9, 2001, Breckenridge, CO.
Ganesh et al., "Cellulase Deactivatioin in a Stirred Reactor," Biochemical Engineering Journal 4 (2000) pp. 137-141.

* cited by examiner

*Primary Examiner*—Sandra E. Saucier
(74) *Attorney, Agent, or Firm*—Fitch, Even, Tabin & Flannery

(57) ABSTRACT

Processes for the production of a product by the enzymatic treatment of a soluble or particulate substrate with a particulate, immobilized enzyme, by treating a process liquor containing the substrate in a bioreactor to produce a slurry of effluent immobilized enzyme and the product in an effluent liquor. The slurry is subject to a non-immobilized enzyme damaging shear inducing effective separation process to provide effluent immobilized enzyme, and effluent liquor containing the product; and reusing the effluent immobilized enzyme in the enzymatic treatment. The process provides for the reclamation and reuse of the immobilized enzyme even when a further particulate solid is present in the effluent/product stream.

4 Claims, 3 Drawing Sheets

RECOVERY METHOD FOR IMMOBILIZED BIOCATALYSTS

RELATED APPLICATION

This U.S. Application claims the foreign priority under 35 U.S.C. §119, including subsections (a)–(d) and (f), from Canadian Application 2,354,782, filed Aug. 2, 2001.

FIELD OF THE INVENTION

This invention relates to the use of immobilized enzymes on a matrix in chemical processes, particularly industrial processes, and more particularly to the recovery of said immobilized enzymes from said process for reuse.

BACKGROUND OF THE INVENTION

The industrial use of enzymes is often limited by their high cost and rapid inactivation. Soluble enzymes are lost with the product at the conclusion of a process, and must be replenished.

One means to improve the economic feasibility of enzymes for industrial processes is through enzyme immobilization onto a matrix, which may facilitate their re-use. Immobilization research has focused upon means to enhance the transfer of enzymes onto the support, and upon means to ensure that the immobilized enzymes remain active. Inactivation of enzymes during catalytic turnover is another key obstacle which limits the economic feasibility of enzyme-mediated processes. Enzymes may be inactivated by extremes of temperature, pH, shear, and also by free radicals and other reactive species present in the reaction medium. Immobilization technology has the potential to reduce such enzyme inactivation, and thus extend their useful lifespans.

Biochemical Engineering Journal, 4, (2000), 137–141, Ganesh K et al, teaches that during the production or downstream processing of an enzyme it is always subjected to shear stress, which may deactivate the enzyme. This susceptibility of enzymes to shear stress is a major concern as it leads to the loss of enzyme activity and is, therefore, a major consideration in the design of the processes involving enzyme production and its application. In this reference, cellulase enzyme was subjected to shear stress in a stirred reactor with an objective of investigating its deactivation under various conditions, such as different agitation speeds, concentrations of enzyme, concentrations of buffer, pH ranges, buffer systems and the presence of gas-liquid interface. It was found that the extent of deactivation depends upon the conditions under which the enzyme was subjected to shear.

For industrial use, it is generally not sufficient for only one of these obstacles to be overcome. For example, a stable, immobilized enzyme that cannot be easily recovered or reused offers few advantages. Similarly, an immobilized enzyme that is easily recovered and reused, but does not maintain its activity over an extended period offers few advantages over a process mediated by soluble enzymes, since, in both cases, the enzymes must be replenished at frequent intervals. The main goals are to produce a stable immobilized enzyme, which can also be efficiently and completely recovered, so that its useful lifespan is many times greater than the single use afforded by a soluble enzyme. An enzyme recovery system is therefore of paramount importance.

To date, immobilized enzyme/reactor technologies have focused on "in situ" enzyme preparations, in which the enzymes are retained within the reactors, while the process fluid is passed through. This prevents loss of the enzyme with the process fluid, and allows the enzyme to be used several times. Examples include, enzymes immobilized within gels which are used within a packed bed reactor, and enzymes attached to, or retained within, semi-permeable, hollow, fiber membranes. Enzymes have also been incorporated within monoliths, such as those used in an automobile catalytic converter, wherein the fluid containing the substrate passes through the monolith.

Unfortunately, enzymes "entrapped" within gels are subject to mass transfer limitations, which may dramatically reduce the performance of the immobilized enzymes, relative to soluble enzymes. The use of enzymes in packed beds is seemingly attractive in that the immobilized enzyme is retained within the reactor, while the process fluid containing substrate and product passes through. However, such an arrangement may be limited by mass transfer outside the particle, due to restriction of fluid flow around the tightly packed particles. To avoid extra-particle mass transfer limitations, relatively large particles are used for the immobilized enzyme. However, larger particles lead to greater mass transfer limitations within the particle, and consequently, it is necessary to choose a particle size that balances intraparticle and extraparticle mass transport. Furthermore, a packed-bed arrangement is only practical if the substrate is easily transported through the packed bed. Replacing the immobilized enzyme in such a reactor may also be time-consuming as to lead to significant process "down-time". Thus, the economic benefits are only realized if the enzyme is very stable, and it does not need frequent replacement.

Packed bed reactors and other types of "in situ" immobilized enzyme reactors, such as monoliths and hollow fibers, can be prone to plugging. Consequently, they may be inappropriate if the substrate is insoluble, for e.g., in a slurry. In all cases, in situ preparations rely on the transport of the substrate to the immobilized enzyme, either by convection or diffusion. If flow is "segregated", as in a slurry, or there is insufficient mixing, or if the substrates are bulky and have low diffusion rates, such substrate-enzyme contact may be hindered and lead to dramatically reduced efficiency and performance. Since some of the key industrial enzymatic processes involve slurries, e.g., starch hydrolysis and pulp processing, there is a need for an immobilized enzyme reactor process that differs from the traditional "in situ" immobilized enzyme reactor.

A particular example of an immobilized enzyme reactor is that which is used for isomerization of dextrose to fructose. A solution of soluble dextrose passes through a bed of immobilized glucose isomerase at such a rate as to ensure a specific product, namely, fructose, concentration at the bed outlet. Owing to continuous inactivation of the immobilized enzyme, the flow rate through the packed bed reactor must be continuously reduced, to ensure that the fructose concentration of the effluent is held constant. It is often necessary to reduce the feed flow rate by a factor of ten or more throughout the "useful" lifespan of the immobilized enzyme. However, such a reduction in flow rate also leads to a proportional reduction in the rate of production of fructose. Consequently, an array of generally 20 or more reactors is used, each of which reactor contains immobilized glucose isomerase of a different age, and each with a different, continuously changing flow rate (H. S. Olsen, Enzymatic Production of Glucose Syrups, in Handbook of Starch Hydrolysis Products and Their Derivatives, M. W. Kearsley and S. Z. Dziedzic, eds., Blackie Academic and Prof. Publishers (Chapman and Hall), Glasgow, 1995). By combining the effluent from each reactor, the average production rate of fructose is kept relatively constant. Once the immobilized enzyme reaches the end of its useful lifespan, that reactor in the array is taken out of service, and the immobilized enzyme is replaced with fresh enzyme.

Unfortunately, such a process arrangement is cumbersome and complex, and the capital cost is high due to the number of reactors required, and the need for complex valving and process control equipment to manage the adjustment of fluid flow rates to each reactor in the array. A further disadvantage of such an arrangement is the production of "color" and other "off-flavor" reversion byproducts, which are more likely to be generated at low flow rates and thus, high residence times. Thus, improvements in immobilized enzyme technology and enzyme recovery methods could dramatically simplify this process, and improve its economics.

U.S. Pat. No. 5,177,005, issued Jan. 5, 1993—Lloyd and Antrim, describes a continuous process for production of fructose involving glucose isomerase adsorbed onto a support such as a resin. The reactor was packed with excess resin as a support and, periodically, fresh, soluble glucose isomerase was added to compensate for the inevitable loss of activity of the previously immobilized enzyme. In trials, fresh glucose isomerase was added approximately every 3 weeks, on average, to keep the dextrose conversion between 40 and 44%. Over a 27 week trial, the quantity of soluble enzyme added represented approximately 4 times the quantity of enzyme originally present in the reactor. Unfortunately, such additions can only continue as long as there is binding capacity on the resin. Once the resin is fully loaded, additional soluble glucose isomerase may confer little benefit, unless the inactivated enzyme is somehow removed from the support. At this point, the process must either be shut down to replace the gel, or run in a "variable flow rate mode", similar to that with traditional immobilized glucose isomerase, described hereinbefore.

U.S. Pat. No. 4,033,820, issued Jul. 5, 1977—Brouillard R. E. describes another in situ immobilized enzyme preparation based on a highly porous, spongy starch gel, modified to act as a support for the enzymes. It was acknowledged that this approach is only suitable for substrates that are soluble in water and that slurries cannot be processed. Another challenge with this approach is the degradation of the starch support gel. Several exotic cross-linking treatments are required if the support is to be used for enzymes that degrade starch, e.g., amylase and glucoamylase. Bactericides, such as formaldehyde or chlorine, were used to regularly wash the column to prevent bacterial contamination.

U.S. Pat. No. 4,209,591, issued Jun. 24, 1980 to Hendriks P., describes a multistage fluidized bed process involving countercurrent flow of an immobilized enzyme and substrate solution. The system is designed such that nearly all of the activity of the immobilized enzyme has been lost by the time it reaches the outlet of the multistage unit. Thus, this operation also involves a "single use" of enzyme, since the enzyme is not recovered or reused. Sieve plates or mesh screens may be used between and within stages to regulate the transfer of immobilized enzyme and substrate from one compartment to the next. In principle, this process is amenable to the use of substrate slurries, however, the particle sizes of the substrate and immobilized enzyme must be small enough to pass through the sieve or mesh. Furthermore, an extremely narrow particle size distribution is required for the immobilized enzyme, to prevent its separation into various sized fractions during operation. It is well accepted that for proper fluidization, the flow rate of the substrate solution is determined in large part by the size and shape of particles and the particle density relative to that of the fluid.

Other examples aimed at multiple use of immobilized enzymes include U.S. Pat. No. 4,442,216, issued Apr. 10, 1984 to Harvey, D. G., U.S. Pat. No. 4,511,654, issued Apr. 16, 1985 to Rohrbach et al, and U.S. Pat. No. 4,594,322, issued Jun. 10, 1986 to Thompson G. J. The former describes a screw-type reactor that includes a screw-lift mechanism and conveyor to recover the immobilized enzyme, wash it and return it to the inlet of the reactor. U.S. Pat. No. 4,511,654 describes an immobilized glucoamylase packed bed reactor with subsequent substrate recycle via an ultrafiltration membrane. The enzyme in this process is, thus, in situ. This process is suitable for soluble sugar feedstocks only. Aforesaid U.S. Pat. No. 4,594,322 describes a similar process in which the hydrolysis products are separated into a glucose-rich stream and a polysaccharide-rich stream, the latter of which is recycled to pass again through the reactor containing immobilized enzyme.

U.S. Pat. No. 4,844,809, issued Jul. 4, 1989 to Yoshiro et al, describes the use of a hollow fiber membrane for removal of fine particles from a reaction solution. While the inventors cite this invention for other purposes, such as the removal of impurities, such a technique could also, conceivably, be used to retain enzymes immobilized to fine particles within a hollow fiber reactor, e.g. "Ultrafiltration Separation of Cellulase and Glucose for a Lignocellulosic Biomass to Ethanol Process", J. S. Knutsen and R. H. Davis, Conference Proceedings, Symposium on Biotechnology for Fuels and Chemicals, Breckenridge, CO, May 6–9, 2001.

Consequently, applications of immobilized enzymes have been essentially restricted to in situ preparations, usually within packed bed reactors. Such processes, although technically and, occasionally economically feasible, may be unnecessarily cumbersome. They may also be unsuitable for process streams in which the substrate is present as a slurry. An immobilized enzyme process capable of processing slurries, and/or which avoids the complexity required to account for enzyme inactivation within in situ preparations, e.g. production of HFCS, would be extremely advantageous.

Slurries cannot be processed using an in situ immobilized enzyme within a packed bed or monolith reactor, due to plugging of the bed or monolith, and mass transfer problems that limit immobilized enzyme-substrate contact. A design in which the immobilized enzyme is free to circulate within the reactor can overcome these limitations. However, a means to facilitate recovery and reuse of the immobilized enzyme is also required.

There is, therefore, a need for an immobilized enzyme recovery process which enables the immobilized enzyme to be reused and, preferably, recycled within a full enzymatic treatment plant, wherein substrate feedstock is enzymatically treated with particulate immobilized enzyme.

SUMMARY OF THE INVENTION

It is the object of the present invention to provide an efficient immobilized enzyme recovery process of use in industrial plants for the enzymatic reaction of substrate materials.

Accordingly, the invention provides in one aspect an improved process for the production of a product by the enzymatic treatment of a substrate with a particulate, immobilized enzyme, comprising treating a process liquor comprising said substrate in a bioreactor to produce a slurry comprising effluent immobilized enzyme and said product in an effluent liquor, the improvement comprising subjecting said slurry to a non-immobilized enzyme damaging shear inducing effective separation process to provide
   a) said effluent immobilized enzyme; and
   b) effluent liquor containing said product; and reusing said effluent immobilized enzyme in a subsequent said enzymatic treatment.

Surprisingly, I have discovered that notwithstanding the teachings of the prior art, immobilized enzymes can be separated out of bioreactor process effluent slurries under "shear-inducing" separation conditions hithertobefore considered to be too violent to provide undamaged enzyme. Thus, the invention provides a practical separation technique. Such a "shear-inducing" separation step includes, for example, hydrocycloning, continuous centrifuging and the like.

In a further aspect, the invention provides such separations when the effluent slurry further comprises one or more other particulate solids.

In yet a further aspect, the invention provides an improved process for the production of a product by the enzymatic treatment of a particulate feed substrate with a particulate immobilized enzyme, said process comprising treating a process liquor comprising a feed slurry of said particulate substrate and said particulate immobilized enzyme in a bioreactor to produce said product in an effluent slurry comprising effluent particulate immobilized enzyme and effluent particulate substrate the improvement wherein said particulate substrate has a particle size distribution different from said particulate immobilized enzyme, and comprising
   (i) subjecting said effluent slurry to a process selected from the group consisting of screening, hydrocycloning and centrifuging to separate said effluent particulate substrate from said effluent slurry to provide (a) said effluent particulate substrate, and (b) a refined slurry comprising said effluent particulate immobilized enzyme in said process liquor;
   (ii) subjecting said refined slurry to a process selected from the group consisting of screening, hydrocycloning and centrifuging to provide (c) said effluent particulate immobilized enzyme and (d) an effluent process liquor; and
   (iii) using said effluent immobilized enzyme in a subsequent said enzymatic treatment.

The process of the invention provides for the recovery and reuse of immobilized enzymes from a process stream, including process streams in which there is a high solids content. Such a process entails separation of the particulate, immobilized enzyme from the process liquid, and may also entail separation of the solid immobilized enzyme from other solids e.g., feed material substrate within the process stream. Such a process facilitates the use of immobilized enzymes for processes in which the substrate is present in a slurry, and also avoids the complexity of processes currently based on in-situ enzyme preparations. The process of this invention leads to efficient recovery and reuse of immobilized enzymes, and thus, allows immobilized enzymes to be used in processes that currently can only use soluble enzymes. This dramatically reduces the cost of enzymatic processing compared to existing soluble and immobilized enzyme processes.

The process according to the invention as hereinabove defined applies to any enzyme immobilized to a particulate support or matrix. Ideally, the support used is a fine powder, with a relatively narrow particle size distribution. However, the use of supports with a broad particle size distribution is also feasible. Since the process stream may contain other particulate solids, the particle characteristics of the immobilized enzyme, e.g., size, density, tendency to aggregate, and the like, must be sufficiently distinct from the particle characteristics of the process stream solids so as to permit their separation.

Preferably, the non-damaging but effective shear-inducing process of use in the practise of the invention is selected from the group consisting of hydrocycloning, continuous centrifuging and combinations thereof.

It will be readily understood to the person skilled in the art that although shear-mediated deactivation of an enzyme in solution and or an immobilized enzyme slurry depends on several coupled parameters, such as, for example, pressure drop, flow rates, residence times, rpm, G-force, vorticity and apparatus size, the skilled person can readily determine acceptable and efficacious process operating conditions for his apparatus in the practise of the invention in order to significantly reduce or eliminate the likelihood of shear-mediated deactivation of the immobilized enzyme. Guidance is also provided for the practise of the present invention in aforesaid Biochemical Engineering Journal, 2000, 137–141, which describes deactivation of the enzyme cellulase in a solution in a stirred reactor. The authors considered mechanical shear (stirring) and interfacial shear (gas-liquid interface), and referred to other cases of shear-mediated deactivation of cellulase. Shear was expressed in terms of a stirring rate, which is typical, rather than an actual shear measurement which would be in $s^-1$, or possibly expressed in units of surface tension as an indicator of interfacial shear.

Surprisingly, I have further discovered that unexpected efficacious enzymatic treatment of a particulate feed substrate with a particulate immobilized enzyme can be performed, notwithstanding the need for two particulate entities to collide in order to react. Accordingly, in a further broad aspect, the invention provides an improved process for the production of a product by the enzymatic treatment of a particulate feed substrate with a particulate, immobilized enzyme, said process comprising treating a process liquor comprising a feed slurry of said substrate and said immobilized enzyme in a bioreactor to produce said product in an effluent slurry comprising effluent immobilized enzyme and effluent substrate the improvement comprising
   (i) subjecting said effluent slurry to a process to separate said effluent substrate from said effluent immobilized enzyme;
   (ii) collecting said effluent immobilized enzyme; and
   (iii) reusing said immobilized enzyme in said enzymatic treatment.

In yet a further aspect, the invention provides an improved process for the production of a product by the enzymatic treatment of a particulate feed substrate with a particulate immobilized enzyme, said process comprising treating a process liquor comprising a feed slurry of said substrate and said immobilized enzyme in a bioreactor to produce said product in an effluent slurry comprising effluent immobilized enzyme and effluent substrate the improvement wherein said substrate has a particle size distribution different from said immobilized enzyme, and comprising
   (i) subjecting said effluent slurry to a process selected from the group consisting of screening, hydrocycloning and centrifuging to separate said effluent substrate from said effluent slurry to provide (a) said effluent substrate, and (b) a refined slurry comprising said effluent immobilized enzyme in said process liquor;
   (ii) subjecting said refined slurry to a process selected from the group consisting of screening, hydrocycloning and centrifuging to provide (c) said effluent immobilized enzyme and (d) an effluent process liquor;

(iii) reusing said effluent immobilized enzyme in said enzymatic treatment.

The aforesaid process, as hereinabove defined, comprises subjecting the slurry to non-immobilized enzyme damaging shear-inducing effective separation steps.

The process of separation and recovery of the immobilized enzyme from the bioreactor process effluent stream may entail one or more steps, depending upon the nature of the process stream. A first step generally involves the separation of the different types of solids within the bioreactor process feed stream, herein named slurry No. 1. Typically, this separation is based on particle size, but is also influenced by other particle characteristics such as, for example, density. This separation produces two solid slurries, one of which contains the immobilized enzyme. The slurry containing the effluent immobilized enzyme, herein named slurry No. 2, is then sent for further processing, in this case, to separate the immobilized enzyme from the process fluid containing product. The immobilized enzyme so separated can then be recycled to the bioreactor, wherein it can be reused for further processing. The slurry containing the other process effluent solids slurry No. 3 can be sent for further processing, or may be subjected to a second solids separation step, in the event that some of the effluent immobilized enzyme from slurry No. 1 has been retained within this stream. The desirability for such supplementary processing steps is influenced by the relative solids loading in slurry No. 1, the densities of the solids, and the particle size distribution of the different solids constituents. If subsequent solids separation is required, the effluent immobilized enzyme recovered from this step may be added to the effluent immobilized enzyme recovered from slurry No. 2, and returned to the enzyme bioreactor.

The practise of the present invention is applicable, for example, to the processes listed in the table below.

| Enzyme | Substrate | Product/process |
| --- | --- | --- |
| Amylase | starch (corn, wheat, barley, rice..) | maltodextrins |
| Amylase | starch | modified starch for pulp sizing |
| Amylase | starch | deinking of coated papers |
| Cellulase | wood pulp/recycled paper | surface-modified pulp/deinked paper |
| Cellulase | cottons | detergents |
| Glucoamylase | dextrins | maltose/glucose |
| Glucose isomerase | glucose | fructose (high fructose corn syrup) |
| Glucose oxidase | glucose | gluconic acid |
| Protease | proteins | detergents |
| Tyrosinase | L-tyrosine | L-DOPA |
| Xylanase | wood pulp/xylan | biobleaching of wood pulp |
| Xylanase | xylan | Xylose |

Examples of processes involving solid substrates and immobilized enzymes include:
(1) amylases used to partially or completely hydrolyze starch to produce either modified starch or dextrins, the latter of which may be subject to further processing to produce simple sugars, (2) cellulases and/or xylanases used to partially or completely hydrolyze pulp fibers, as in enzymatic deinking, biobleaching, fiber modification, or glucose/xylose production, for subsequent fermentation, and (3) cellulases, lipases, or proteases used in detergents for fiber modification and/or stain removal.

Examples of processes involving soluble substrates and immobilized enzymes include glucose oxidase used to convert glucose to gluconic acid, glucoamylase used to convert dextrins to monosacharrides, glucose isomerase used to produce high fructose corn syrups from glucose, tyrosinase used to produce L-DOPA from L-tyrosine or to convert other mono- or di-phenolics in wastewater streams, and enzymes such as lipases used to produce nutraceuticals.

BRIEF DESCRIPTION OF THE DRAWINGS

In order that the invention may be better understood, preferred embodiments will now be described, by way of example only, with reference to the accompanying drawings, wherein.

DETAILED DESCRIPTION OF PREFERRED EMBODIMENTS

EXAMPLE 1

Figure 1:
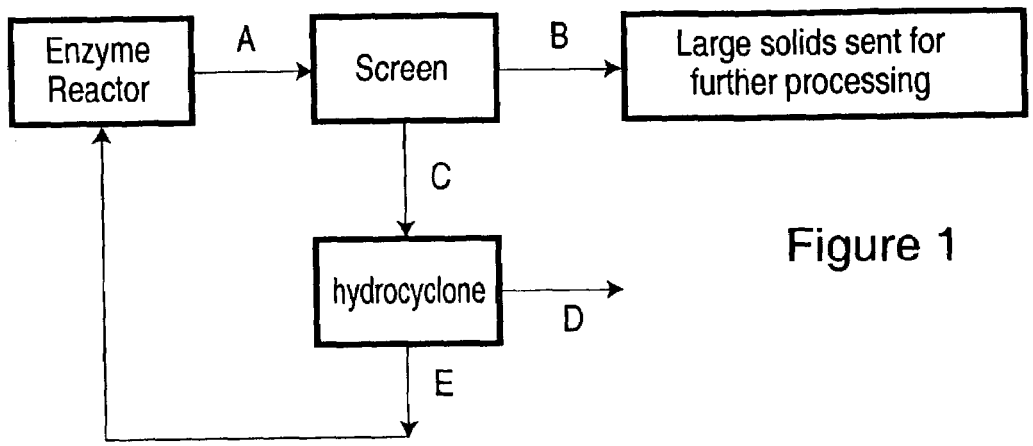
FIGS. 1–5 represent process flow charts of various embodiments of processes according to the invention.

Reference is now made to FIG. 1 wherein the process steps are as listed hereinbelow.

A=Process stream (slurry) containing immobilized enzyme and other process solids B=Overflow, primarily large solids with very little process liquid C=Underflow, comprised of fine solids and most of the process liquid from stream A D=overflow, comprised almost entirely of process liquid E=underflow, comprised of fine solids and a small portion of process liquid.

The flow diagram of FIG. 1 is based on the premise that the immobilized enzyme is present as a fine solid, while the other process solids are present as much larger particles. This implies that stream C contains the immobilized enzyme to ultimately be recycled to the reactor for use in a subsequent enzymatic reaction. Should the opposite be true, stream B would contain the immobilized enzyme, which would then be recycled, and the solid separation of stream C provided via the hydrocyclone may not be necessary.

A mixture of 30% corn mash (mean 700 µm; 98%>350 µm) and 1.33% immobilized enzyme (mean 18 µm; range 1 to 120 µm) was processed according to FIG. 1. A 355 µm mesh screen was used to separate the two solids. 95% of the corn mash and 7% of the immobilized enzyme proceeded to the overflow (stream B). The balance (as stream C) proceeded to a manifolded set of 10 mm hydrocyclones with a 2.5 mm (dia) inlet. 65% of the solids in stream C were directed to the underflow (stream E), and 35% proceeded to stream D, based on a pressure drop of 2.7 bar across each hydrocyclone, and a flow rate of 2.8 L/min/cyclone. 78% of the process fluid in stream C was directed to stream D. The total recovery of immobilized enzyme under these conditions was, thus, 60%.

EXAMPLE 2

With reference to FIG. 1 wherein the process steps are as listed hereinbelow.
A=Process stream (slurry) containing immobilized enzyme and other process solids
B=Overflow, primarily large solids with very little process liquid
C=Underflow, comprised of fine solids and most of the process liquid from stream A
D=overflow, comprised almost entirely of process liquid
E=underflow, comprised of fine solids and a small portion of process liquid.

This flow diagram is based on the premise that the immobilized enzyme is present as a fine solid, while the other process solids are present as much larger particles. This implies that stream C contains the immobilized enzyme to ultimately be recycled to the reactor. Should the opposite be true, stream B would contain the immobilized enzyme, which would then be recycled, and the solid separation of stream C provided via the hydrocyclone may not be necessary.

A mixture of 30% corn mash (mean 700 μm; 98%>350 μm) and 2.67% immobilized enzyme (mean 18 μm; range 1 to 120 μm) was processed according to FIG. 1. A 355 μm mesh screen was used to separate the two solids. 90% of the corn mash and 6% of the immobilized enzyme proceeded to the overflow (stream B). The balance (as stream C) proceeded to a manifolded set of 10 mm hydrocyclones with a 2.5 mm (dia) inlet. 81% of the solids in stream C were directed to the underflow (stream E), and 19% proceeded to stream D, based on a pressure drop of 2.7 bar across each hydrocyclone, and a flow rate of 2.8 L/min/cyclone. 73% of the process fluid was directed to stream D. The total recovery of immobilized enzyme under these conditions was 76%.

EXAMPLE 3

With reference to FIG. 1 wherein the process steps are as listed hereinbelow.
A=Process stream (slurry) containing immobilized enzyme and other process solids
B=Overflow, primarily large solids with very little process liquid
C=Underflow, comprised of fine solids and most of the process liquid from stream A
D=overflow, comprised almost entirely of process liquid
E=underflow, comprised of fine solids and a small portion of process liquid.

This flow diagram is based on the premise that the immobilized enzyme is present as a fine solid, while the other process solids are present as much larger particles. This implies that stream C contains the immobilized enzyme to ultimately be recycled to the reactor. Should the opposite be true, stream B would contain the immobilized enzyme, which would then be recycled, and the solid separation of stream C provided via the hydrocyclone may not be necessary.

A mixture of 30% corn mash (mean 700 μm; 98%>350 μm) and 2.0% immobilized enzyme (mean 18 μm; range 1 to 120 μm) was processed according to FIG. 1. A 250 μm mesh screen was used to separate the two solids. 100% of the corn mash and 4% of the immobilized enzyme proceeded to the overflow (stream B). The balance (as stream C) proceeded to a manifolded bank of 10 mm hydrocyclones with a 2.5 mm (dia) inlet. 71% of the solids in stream C were directed to the underflow (stream E), and 29% proceeded to stream D, based on a pressure drop of 2.7 bar across each hydrocyclone, and a flow rate of 2.8 L/min/cyclone. 82% of the fluid in stream C was directed to stream D, and 18% of the fluid went to stream E. The total immobilized enzyme recovery under these conditions was 68%.

EXAMPLE 4

Figure 4:
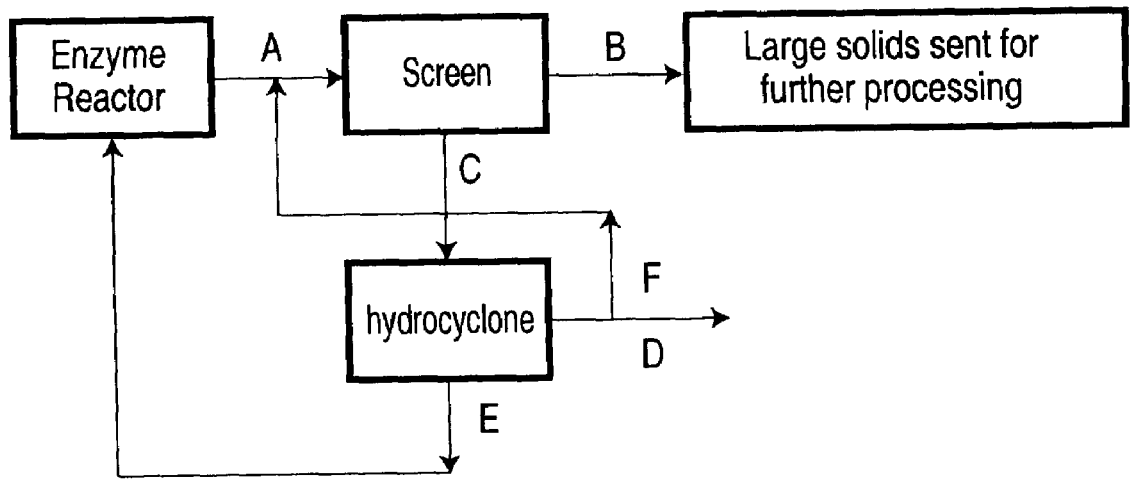

With reference to FIG. 4 wherein the process steps are as listed hereinbelow.
A=Process stream (slurry) containing immobilized enzyme and other process solids
B=overflow, primarily large solids with very little process liquid
C=underflow, comprised of fine solids and most of the process liquid from stream A
D=overflow, comprised almost entirely of process liquid
E=underflow, comprised of fine solids and a small fraction of the liquid from stream C.
F=process liquid for recycle This flow diagram is based on the premise that the immobilized enzyme is present as a fine solid, while the other process solids are present as much larger particles. This implies that stream C contains the immobilized enzyme to ultimately be recycled to the reactor. Should the opposite be true, stream B would contain the immobilized enzyme, which would then be recycled. The solid separation of stream C provided via the hydrocyclone may be required to dilute the solids present in stream A, facilitating the separation of fine and coarse solids via the screen.

A mixture of 30% corn mash (mean 700 μm; 98%>350 μm) and 2.0% immobilized enzyme (mean 25 μm; range 5 to 90 μm) was processed according to FIG. 4. After dilution, the feed to the screen contained 15% corn mash and 1% immobilized enzyme. A 250 μm mesh screen was used to separate the two solids. 100% of the corn mash and 1% of the immobilized enzyme proceeded to the overflow (stream B). The balance (as stream C) proceeded to a manifolded bank of 10 mm hydrocyclones with a 2.5 mm (dia) inlet. 78% of the solids in stream C were directed to the underflow (stream E), and 22% proceeded to stream D, based on a pressure drop of 2.7 bar across each hydrocyclone, and a flow rate of 2.8 L/min/cyclone. 72% of the fluid in stream C was directed to stream D, and 28% of the fluid went to stream E. The total immobilized enzyme recovery under these conditions was 77%.

EXAMPLE 5

Figure 2:
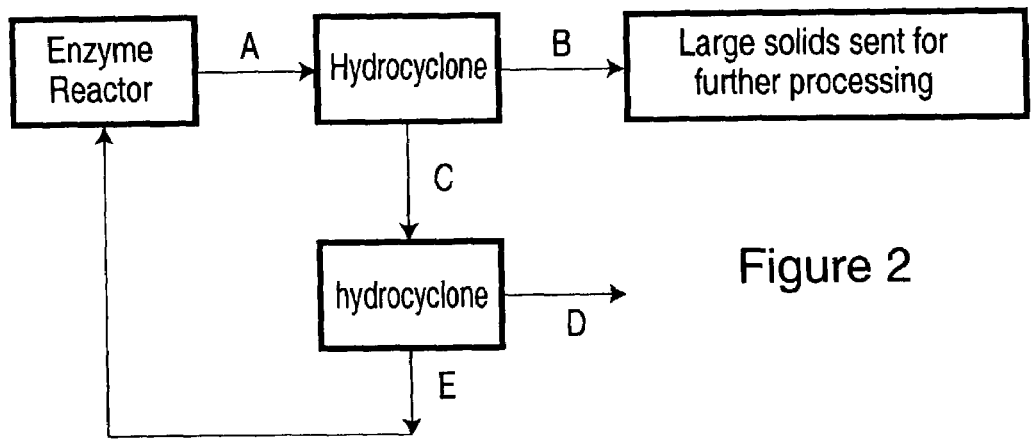

With reference to FIG. 2 wherein the process steps are as listed hereinbelow.
A=Process stream (slurry) containing immobilized enzyme and other process solids
B=underflow, primarily large solids with some process liquid
C=overflow, comprised of fine solids and 50–80% of the process liquid from stream A
D=overflow, comprised almost entirely of process liquid
E=underflow, comprised of fine solids and a small fraction of the liquid from stream C.

This flow diagram is based on the premise that the immobilized enzyme is present as a fine solid, while the other process solids are present as much larger particles. This implies that stream C contains the immobilized enzyme to ultimately be recycled to the reactor. Should the opposite be true, stream B would contain the immobilized enzyme, which would then be recycled, and the solid separation of stream C provided via the hydrocyclone may not be necessary.

A mixture of 30% corn mash (mean 700 μm; 98%>350 μm) and 1% immobilized enzyme (mean 18 μm; range 1 to 120 μm) was processed according to FIG. 2. A hydrocyclone with a 3 cm (dia) inlet was used to separate the two solids. The feed rate was 6.6 L/s, and the pressure drop across the hydrocyclone was 0.5 bar. 100% of the corn mash and 29% of the immobilized enzyme proceeded to the underflow (stream B). The balance (as stream C) proceeded to a manifolded set of 10 mm hydrocyclones with a 2.5 mm (dia) inlet. 78% of the solids in stream C were directed to the underflow (stream E), and 22% proceeded to stream D, based on a pressure drop of 3.4 bar across each hydrocyclone, and a flow rate of 9.4 L/min/cyclone. The total recovery of immobilized enzyme under these conditions was thus 55%.

EXAMPLE 6

Figure 3:
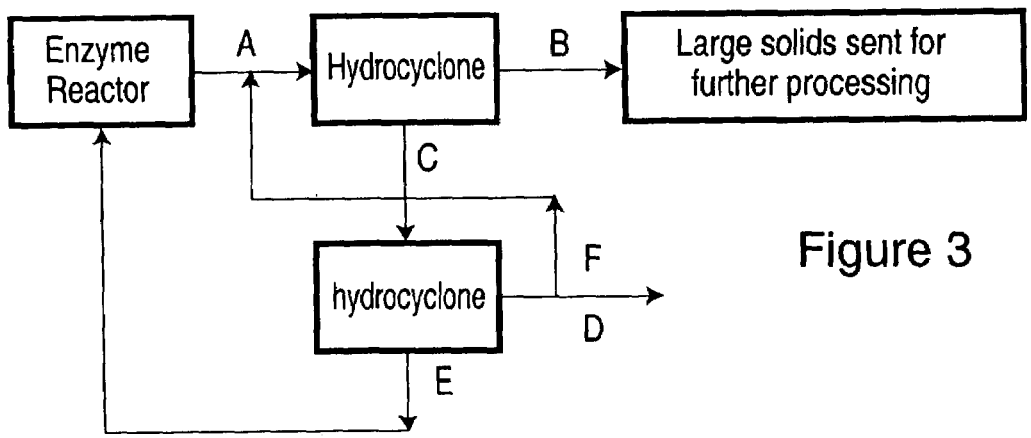

With reference to FIG. 3 wherein the process steps are as listed hereinbelow.
A=Process stream (slurry) containing immobilized enzyme and other process solids
B=underflow, primarily large solids with some process liquid
C=overflow, comprised of fine solids and 50–80% of the process liquid from stream A
D=overflow, comprised almost entirely of process liquid
E=underflow, comprised of fine solids and a small fraction of the liquid from stream C.
F=process liquid for recycle This flow diagram is based on the premise that the immobilized enzyme is present as a fine solid, while the other process solids are present as much larger particles. This implies that stream C contains the immobilized enzyme to ultimately be recycled to the reactor. Should the opposite be true, stream B would contain the immobilized enzyme, which would then be recycled, and the solid separation of stream C provided via the hydrocyclone may not be necessary.

A mixture of 30% corn mash (mean 700 μm; 98%>350 μm) and 1.33% immobilized enzyme (mean 18 μm; range 1 to 120 μm) was processed according to FIG. 3, with sufficient fluid recycle (stream F) to reduce the solids loading to the first hydrocyclone to ~20%. A hydrocyclone with a 3 cm (dia) inlet was used to separate the two solids. The feed rate was 10.1 L/s, and the pressure drop across the hydrocyclone was 0.5 bar. 100% of the corn mash and 18% of the immobilized enzyme proceeded to the underflow (stream B). The balance (as stream C) proceeded to a manifolded set of 10 mm hydrocyclones with a 2.5 mm (dia) inlet. 78% of the solids in stream C were directed to the underflow (stream E), and 22% proceeded to stream D, based on a pressure drop of 2.7 bar across each hydrocyclone, and a flow rate of 2.8 L/min/cyclone. The total recovery of immobilized enzyme under these conditions was, thus, 64%.

EXAMPLE 7

Figure 5:
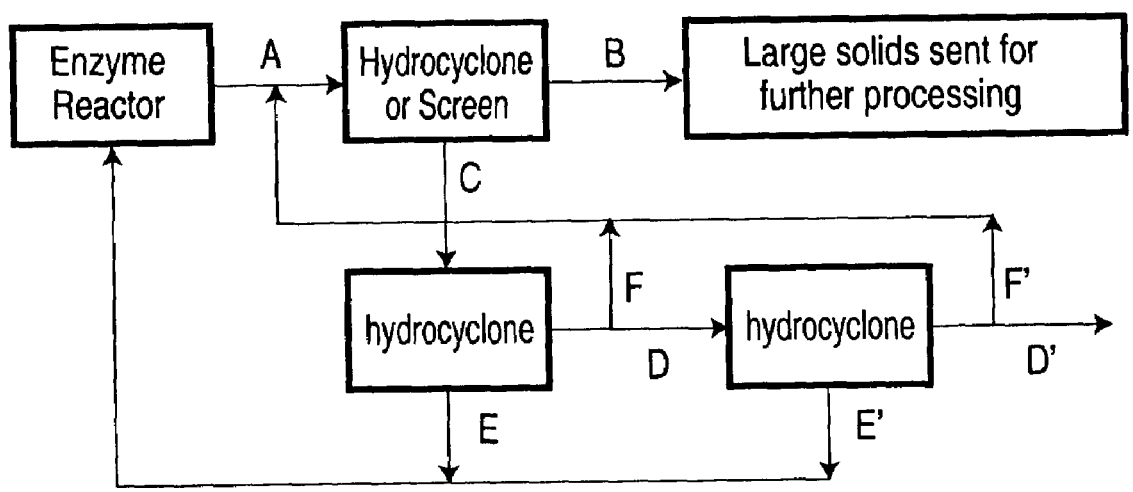

With reference to FIG. 5 wherein the process steps are as listed hereinbelow.
A=Process stream (slurry) containing immobilized enzyme and other process solids
B=underflow, primarily large solids with some process liquid
C=overflow, comprised of fine solids and 50–80% of the process liquid from stream A
D=overflow, comprised almost entirely of process liquid
E=underflow, comprised of fine solids and a small fraction of the liquid from stream D.
F=process liquid for recycle
D'=overflow, comprised almost entirely of process liquid
E'=underflow, comprised of fine solids and a small fraction of the liquid from stream C.
F'=process liquid for recycle This flow diagram is based on the premise that the immobilized enzyme is present as a fine solid, while the other process solids are present as much larger particles. This implies that stream C contains the immobilized enzyme to ultimately be recycled to the reactor. Should the opposite be true, stream B would contain the immobilized enzyme, which would then be recycled, although the solid separation of streams C and D via the hydrocyclones may be needed to produce recycle fluid to dilute the solids in stream A.

Note that FIG. 5 differs from FIG. 3 only by the fact that an additional hydrocyclone is added to improve the separation/recovery of fine particles, and to increase the percentage of process fluid recycled to mix with stream A. As required, additional hydrocyclones/centrifuges beyond the two shown here can be incorporated into the process, adding to the fluid recycle streams F and F', and solid recycle streams E and E'.

A mixture of 30% corn mash (mean 700 μm; 98%>350 μm) and 1.33% immobilized enzyme (mean 18 μm; range 1 to 120 μm) was processed according to FIG. 5, with sufficient fluid recycle (streams F and F') to reduce the solids loading to the first hydrocyclone to ~10%. A hydrocyclone with a 4.8 cm (dia) inlet was used to separate the two solids. The feed rate was 21 L/s, and the pressure drop across the hydrocyclone was 0.5 bar. 100% of the corn mash and 8% of the immobilized enzyme proceeded to the underflow (stream B). The balance (as stream C) proceeded to a manifolded set of 10 mm hydrocyclones with a 2.5 mm (dia) inlet. 78% of the solids in stream C were directed to the underflow (stream E), and 22% proceeded to stream D, based on a pressure drop of 2.7 bar across each hydrocyclone, and a flow rate of 2.8 L/min/cyclone. A second set of hydrocyclones was used to separate the solids in stream D, directing 70% of the solids to the underflow (stream E'), and 30% to the overflow (stream F'). For each of these latter two hydrocyclones, 73% of the fluid was directed to the overflow (streams F and F'), and 23% was directed to the underflow (E and E'). The total recovery of immobilized enzyme under these conditions was thus 86%.

EXAMPLE 8

With reference to FIG. 1 wherein the process steps are as listed hereinbelow.
A=Process stream (slurry) containing immobilized enzyme and other process solids
B=Overflow, primarily large solids with very little process liquid
C=Underflow, comprised of fine solids and most of the process liquid from stream A
D=overflow, comprised almost entirely of process liquid
E=underflow, comprised of fine solids and a small portion of process liquid.

This flow diagram is based on the premise that the immobilized enzyme is present as a fine solid, while the other process solids are present as much larger particles. This implies that stream C contains the immobilized enzyme to ultimately be recycled to the reactor. Should the opposite be true, stream B would contain the immobilized enzyme, which would then be recycled, and the solid separation of stream C provided via the hydrocyclone may not be necessary.

A mixture of 30% corn mash (mean 700 µm; 98%>350 µm) and 2.66% immobilized enzyme (mean 140 µm; range 1 to 220 µm; median 120 µm) was processed according to FIG. 1. A 355 µm mesh screen was used to separate the two solids. 99% of the corn mash and 1% of the immobilized enzyme proceeded to the overflow (stream B). The balance (as stream C) proceeded to a manifolded set of 10 mm hydrocyclones with a 2.5 mm (dia) inlet. 96% of the solids in stream C were directed to the underflow (stream E), and 4% proceeded to stream D, based on a pressure drop of 2.7 bar across each hydrocyclone, and a flow rate of 2.8 L/min/cyclone. 71% of the process fluid in stream C was directed to stream D. The total recovery of immobilized enzyme under these conditions was, thus, 95%.

EXAMPLE 9

Diluted Feed

A mixture of 17% corn mash (mean 750 µm; 85%>350 µm) and 1.33% immobilized enzyme (mean 120 µm; range 75 to 200 µm) was processed according to FIG. 1, at a feed rate of 225 L/min. A screen with d50=186 µm was used to separate the solids. Ninety percent of the solids <355 µm proceeded to the underflow (stream C), with 6% of the immobilized enzyme lost to the overflow (stream B). Stream C was processed as a batch through a manifolded set of fifteen 10 mm hydrocyclones, with a pressure drop of 5.4 bar across each hydrocyclone, and a flowrate of 181 L/min. Seventy percent of the process fluid was directed to stream D, and 54% of the solids in stream C were directed to stream E. The total recovery of immobilized enzyme under these conditions was 50%.

EXAMPLE 10

Double Deck Screen

A stream containing 35% solids (96% corn mash) was processed according to FIG. 1, with double decked screens. The top screen has a d50=562 µm, and the bottom screen has a d50 of 294 µm. The solids are thus subject to a "rough" cut on the top screen, and a "fine" cut on the bottom screen. Eighty nine percent of the solids <355 µm proceeded to stream C, and 12% of the immobilized enzyme was lost to stream B. Stream C was subsequently processed at 132 L/min, with a pressure drop of 5.6 bar; 87% of the fluid was directed to overflow stream D. The total recovery of immobilized enzyme was 69%.

EXAMPLE 11

Two Stage Screen

A stream containing 35% solids (96% corn mash) was processed according to FIG. 1, modified to use two screens arranged in series on shakers inclined at 30 degrees with respect to horizontal. The first screen had a d50 of 863 µm, and the second screen had a d50 of 387 µm. The solids are thus subject to a "rough" cut on the first screen, and a "fine" cut on the second screen. The feed rate was 132 L/min to the first screen; the screen unders were allowed to accumulate and then fed to the second screen at a rate of 107 L/min. Eighty seven percent of the solids <355 µm and ninety four percent of the immobilized enzyme were ultimately directed to stream C for separation via the hydrocyclones, as described in Example 2, hereinabove. The total recovery of immobilized enzyme was 90%.

EXAMPLE 12

Soluble Substrate Stream

An immobilized enzyme was recovered from a soluble substrate stream according to essentially FIG. 1, without the screen. The loading of immobilized enzyme was 2.1 g/L. The suspension was fed to a manifolded set of fifteen 10 mm hydrocyclones, at a rate of 147 L/min, with a pressure drop of 3.8 bar. Approximately four percent of the fluid was directed to the hydrocyclone underflow, wherein the solids concentration was 56 g/L. The recovery of immobilized enzyme was thus 97%.

EXAMPLE 13

Recycle Operation

A stream containing 30% solids (97% corn mash) was processed according to FIG. 4. The screen had a d50 of 387 µm. Slurry was fed at a rate of 93 L/min, leading to a screen unders flowrate stream C of 140 L/min with a stream F recycle rate of 76 L/min. Eight percent of the solids <355 mm were lost to stream B, which included 5% of the immobilized enzyme. Eighty eight percent of the <250 µm solids in stream C were recovered in stream E.

EXAMPLE 14

Dynamic Drainage Jar

A stream containing 1% hardwood pulp and 0.5 g/L immobilized cellulase (mean diameter 6 µm) was mixed at 800 rpm. The suspension was then rapidly drained through a 100 µm screen. Eighty five percent of the immobilized enzyme was recovered in the underflow/filtrate.

EXAMPLE 15

Large Particle Immobilized Enzyme

A mixture of 22% corn mash (mean 650 µm; 93%>350 µm) and 1.6% immobilized enzyme (range 850 to 1200 µm) was processed according to FIG. 1, at a feed rate of 50 L/min. An 850 µm screen was used to separate the solids. Virtually all of the solids >850 µm proceeded to the overflow (stream B); only 0.02% of the solids in stream C were larger than 850 µm. This implies that there was essentially 100% recovery of the immobilized enzyme in stream B. Stream C was sent for further processing, while stream B, with the immobilized enzyme, was recycled for further use.

EXAMPLE 16

Two examples, hereinbelow denoted 16A and 16B describe experiments to establish effect of shear on enzymes.

Description of experiments:

Equipment and materials

The equipment consisted of a 250 L feed tank with mixer, a positive displacement pump (maximum 6.8 bar discharge, capacity up to 22 L/min), and a manifolded set of six hydrocyclones (10 mm, with a 2.5 mm (dia) inlet). The piping was arranged to return the fluid from the overflow and underflow of the hydrocyclone to the feed tank, so that the apparatus was run under a continuous recycle. The feed tank was initially filled with 150 L of soluble enzyme; a sample of this solution was collected for a subsequent activity assay. In the first experiment, Spezyme® enzyme from Genencor International was used, and in the second experiment, Liquozyme® enzyme from Novozymes was used. The activity of each α-amylase was determined using a reducing sugars assay, using corn flour as the substrate.

Procedure:

An aforesaid soluble enzyme was pumped through the hydrocyclones at a rate of 16 L/min, with a pressure drop of 2.7 bar between the inlet and the outlets. Seventy percent of the fluid was directed to the overflow, and thirty percent was directed to the underflow. Samples of the soluble enzyme were collected at regular intervals, and assayed for enzyme activity, as follows:

1.0 mL of enzyme sample was added to 24.0 mL of buffer either pH 6.9 for Spezyme® enzyme, or pH 5.0 for Liquozyme® enzyme. The reaction was initiated by adding 0.20 g of corn flour. Samples were collected at time zero, and every 3 minutes for 15 minutes. Samples were centrifuged to precipitate any suspended corn flour. 1.5 mL of the supernatant was mixed with 3 mL of dinitrosalicylic acid reagent in a test tube, and cooked for 5 minutes in a boiling water bath. The mixture was then cooled to room temperature, and the absorbance was determined at 540 nm.

Results

16A

1) Experiments with Spezyme® Enzyme

Figure 6:
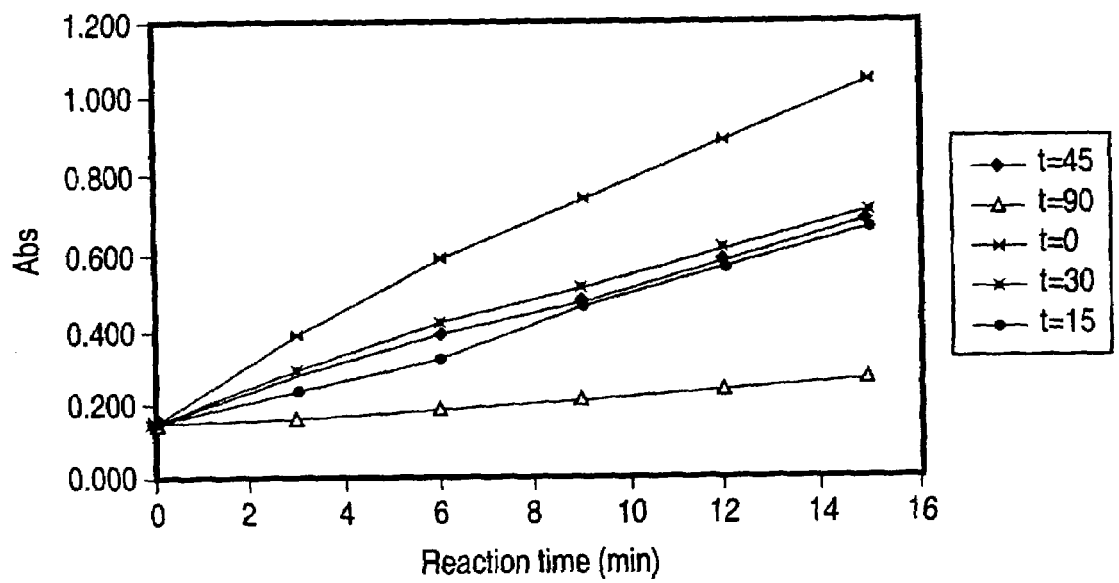
FIG. 6 represents a graph of hydrocyclone assays with spezyme® soluble enzyme.

The results from experiments with Spezyme® enzyme are presented in FIG. 6. The data show that processing the soluble enzyme through the hydrocyclone leads to approximately a 40% reduction in activity within 15 minutes, and approximately a 75% reduction in activity after 90 minutes. In contrast, under normal storage conditions, the enzyme is expected to remain active over a period of 4 to 6 months (manufacturer's technical sheet).

16B

2) Experiments with Liquozyme® Enzyme

The results from experiments with Liquozyme® enzyme are presented in FIG. 7, below. The data show that processing the soluble enzyme through the hydrocyclone leads to approximately a 25% reduction in activity within 15 minutes, but no further loss of activity thereafter. In contrast, under normal storage conditions, the enzyme is expected to remain active over 4 to 6 months (manufacturer's technical sheet).

Figure 7:
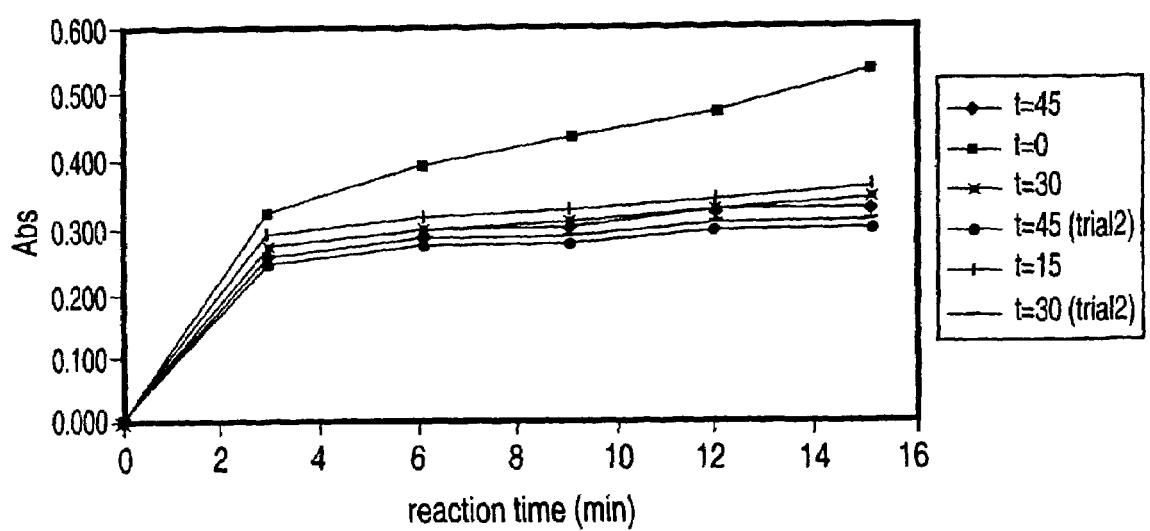
FIG. 7 represents a graph of hydrocyclone assays with liquozyme® soluble enzyme; and when the same letters denote like parts and process steps.

Thus, it can be seen that the shear results shown in FIGS. 6 and 7 for the processing of these soluble enzymes through the hydrocyclone system, leads to a rapid loss of activity, although, Liquozyme® enzyme is less sensitive to shear inactivation than Spezyme® enzyme.

Although this disclosure has described and illustrated certain embodiments of the invention, it is to be understood that the inventions is not restricted to those particular embodiments. Rather, the invention includes all embodiments which are functional or mechanical equivalence of the specific embodiments and features that have been described and illustrated.

The invention claimed is:

1. A process for producing a product by enzymatic treatment of a particulate substrate comprising:
   providing a particulate feed substrate,
   providing a particulate, immobilized enzyme,
   reacting the particulate feed substrate with the particulate, immobilized enzyme in a bioreactor to produce an effluent process liquor containing the effluent particulate, immobilized enzyme, a product of the reaction and an effluent particulate substrate, which has a particle size distribution different from the effluent particulate, immobilized enzyme,
   treating the process liquor to produce a slurry,
   subjecting the slurry to at least one of screening, continuous centrifuging or hydrocycloning to separate the effluent particulate substrate from the effluent particulate, immobilized enzyme,
   subjecting the slurry to hydrocycloning to separate the particulate, immobilized enzyme from the product, and
   recycling the particulate, immobilized enzyme.

2. The method of claim 1, wherein the particulate feed substrate is corn mash.

3. The method of claim 1, wherein the particulate feed substrate is cellulosic feed stock.

4. The method of claim 1, wherein the particulate feed substrate is hemicellulosic feed stock.

* * * * *